US009084545B2

(12) United States Patent
Sullivan et al.

(10) Patent No.: US 9,084,545 B2
(45) Date of Patent: Jul. 21, 2015

(54) FILTER MECHANISM FOR REMOVING ECG ARTIFACT FROM MECHANICAL CHEST COMPRESSIONS

(71) Applicant: Physio-Control, Inc., Redmond, WA (US)

(72) Inventors: Joseph L. Sullivan, Kirkland, WA (US); Robert Marx, Kent, WA (US); Robert G. Walker, Seattle, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 0 days.

(21) Appl. No.: 13/676,593

(22) Filed: Nov. 14, 2012

(65) Prior Publication Data

US 2013/0296727 A1 Nov. 7, 2013

Related U.S. Application Data

(60) Provisional application No. 61/642,407, filed on May 3, 2012.

(51) Int. Cl.
*A61N 1/08* (2006.01)
*A61B 5/04* (2006.01)
(Continued)

(52) U.S. Cl.
CPC ............. *A61B 5/04017* (2013.01); *A61B 5/046* (2013.01); *A61B 5/7217* (2013.01); *A61H 31/005* (2013.01); *A61H 31/006* (2013.01); *A61N 1/3925* (2013.01); *A61H 2201/5007* (2013.01); *A61H 2201/5043* (2013.01); *A61H 2201/5097* (2013.01);
(Continued)

(58) Field of Classification Search
USPC ........................................ 607/60; 601/41–42
See application file for complete search history.

(56) References Cited

U.S. PATENT DOCUMENTS 5,687,735 A 11/1997 Forbes et al.
6,752,771 B2 * 6/2004 Rothman et al. ................ 601/44
(Continued)

FOREIGN PATENT DOCUMENTS

WO 2009071128 6/2009

OTHER PUBLICATIONS

Dotsinsky I, Suppression of AC railway power-line interference in ECG signals recorded by public access defibrillators, BioMedical Engineering OnLine (2005) 4:65.
(Continued)

*Primary Examiner* — Rex R Holmes
(74) *Attorney, Agent, or Firm* — Marger Johnson & McCollom PC

(57) ABSTRACT

An external medical device can include a housing and a processor within the housing. The processor can be configured to receive an input signal for a patient receiving chest compressions from a mechanical chest compression device. The processor can also be configured to select at least one filter mechanism, the mechanical chest compression device having a chest compression frequency f. The processor can be further configured to apply the at least one filter mechanism to the signal to at least substantially remove chest compression artifacts from the signal, wherein the chest compression artifacts correspond to the chest compressions being delivered to the patient by the mechanical chest compression device, and wherein the at least one filter mechanism substantially rejects content in the frequency f plus content in at least one more frequency that is a higher harmonic to the frequency f.

37 Claims, 14 Drawing Sheets

*DEFIBRILLATION SCENE*

(51) Int. Cl.
    *A61B 5/00* (2006.01)
    *A61N 1/39* (2006.01)
    *A61H 31/00* (2006.01)
    *A61B 5/046* (2006.01)

(52) U.S. Cl.
    CPC .... *A61H 2230/045* (2013.01); *A61H 2230/206* (2013.01); *A61H 2230/208* (2013.01); *A61H 2230/305* (2013.01)

(56) References Cited

U.S. PATENT DOCUMENTS

| | | |
|---|---|---|
| 7,039,457 B2 | 5/2006 | Young et al. |
| 7,220,235 B2 | 5/2007 | Geheb et al. |
| 7,565,194 B2 | 7/2009 | Tan et al. |
| 7,567,837 B2 | 7/2009 | Weil et al. |
| 7,650,181 B2 | 1/2010 | Freeman et al. |
| 7,831,299 B2 | 11/2010 | Tan et al. |
| 2002/0165471 A1 | 11/2002 | Halperin |
| 2005/0101889 A1 | 5/2005 | Freeman et al. |
| 2005/0137628 A1 | 6/2005 | Young et al. |
| 2005/0256415 A1 | 11/2005 | Tan et al. |
| 2006/0025824 A1 | 2/2006 | Freeman et al. |
| 2006/0149157 A1 | 7/2006 | Weil et al. |
| 2006/0235320 A1 | 10/2006 | Tan et al. |
| 2006/0258927 A1 | 11/2006 | Edgar et al. |
| 2007/0100379 A1 | 5/2007 | Tan et al. |
| 2007/0162076 A1 | 7/2007 | Tan et al. |
| 2010/0076510 A1 | 3/2010 | Lyster |
| 2011/0034816 A1 | 2/2011 | Tan et al. |
| 2011/0105930 A1 | 5/2011 | Thiagarajan et al. |
| 2011/0202100 A1 | 8/2011 | Tan et al. |
| 2011/0202101 A1 | 8/2011 | Tan et al. |
| 2012/0010543 A1 | 1/2012 | Johnson et al. |
| 2012/0016279 A1 | 1/2012 | Banville et al. |
| 2012/0157865 A1 | 6/2012 | Stein et al. |
| 2013/0184600 A1* | 7/2013 | Tan et al. ............ 600/518 |
| 2014/0088374 A1* | 3/2014 | Sullivan et al. ......... 600/301 |

OTHER PUBLICATIONS

Dotsinsky I, Neycheva T, Fast electrocardiogram amplifier recovery after a defibrillation shock, Bioautomation (2005) 2:76-84.

Ruiz J et al, Cardiopulmonary resuscitation artefact suppression using a Kalman filter and the frequency of chest compressions as the reference signal, Resuscitation 81 (2010) 1087-1094.

Aramendi et al, Detection of ventricular fibrillation in the presence of cardiopulmonary resuscitation artefacts, Resuscitation (2007) 72:115-123.

Lee B et al, Adaptive comb filtering for motion artifact reduction from PPG with a structure of adaptive lattice IIR notch filter, 33rd Annual International Conference of the IEEE EMBS, Boston, MA, Aug. 30-Sep. 3, 2011, 4 pages.

Granegger M et al, Use of independent component analysis for reducing CPR artefacts in human emergency ECGs, Resuscitation (2011) 82: 79-84.

Irusta U et al, A least mean-square filter for the estimation of the cardiopulmonary resuscitation artifact based on the frequency of the compressions, IEEE Trans Biomed Eng (2009) 56:21052-62.

Ruiz de Gauna et al, A method to remove CPR artefacts from human ECG using only the recorded ECG, Resuscitation (2008) 76, 271-278.

Aramendi et al, Suppression of the cardiopulmonary resuscitation artefacts using the instantaneous chest compression rate extracted from the thoracic impedance, Resuscitation 83 (2012) 692-698.

Berger et al, Rhythm discrimination during uninterrupted CPR using motion artifact reduction system, Resuscitation (2007) 75, 145-152.

Aramendi, et al.; "A simple effective filtering method for removing CPR cause artefacts from surface ECG signals"; Computers in Cardiology; 2005; pp. 547-550.

International Search Report and Written Opinion; Patent Cooperation Treaty; Oct. 1, 2013; 22 pages; PCT/US2013/039555, European Patent Office.

* cited by examiner

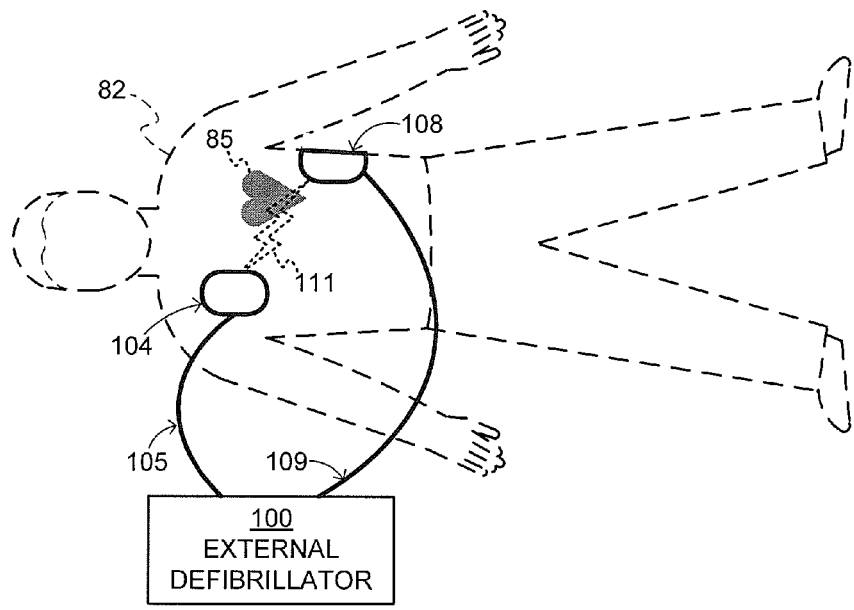
FIG. 1  DEFIBRILLATION SCENE
| TYPE OF EXTERNAL DEFIBRILLATOR | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | √ | |
| AED | √ | √ |
FIG. 2  TWO MAIN TYPES OF EXTERNAL DEFIBRILLATORS

COMPONENTS OF EXTERNAL DEFIBRILLATOR

FIG. 4  *COMPONENTS OF PATIENT ECG SIGNAL MONITORING SYSTEM*

FIG. 5 *FAST FOURIER TRANSFORM OF ECG SIGNAL FROM ASYSTOLIC PATIENT RECEIVING CHEST COMPRESSIONS FROM CONVENTIONAL MECHANICAL CPR DEVICE*

FIG. 6 *FAST FOURIER TRANSFORM OF ECG SIGNAL FROM ASYSTOLIC PATIENT RECEIVING CHEST COMPRESSIONS FROM MECHANICAL CPR DEVICE HAVING PRECISE FREQUENCY CONTROL*

FIG. 7 *FREQUENCY RESPONSE OF A COMB FILTER TO REMOVE CHEST COMPRESSION ARTIFACTS FROM ECG SIGNAL*

FIG. 8 — *FREQUENCY RESPONSE OF AN INVERSE COMB FILTER TO REMOVE CHEST COMPRESSION ARTIFACTS FROM ECG SIGNAL*

SAMPLE PATIENT ECG DATA

SAMPLE ECG SIGNAL HAVING QRS COMPLEXES AND NO CHEST COMPRESSION ARTIFACTS

SAMPLE ECG SIGNAL HAVING QRS COMPLEXES AND CHEST COMPRESSION ARTIFACTS WITH NO FILTERING

SAMPLE ECG SIGNAL HAVING QRS COMPLEXES AND CHEST COMPRESSION ARTIFACTS WITH FILTER APPLIED

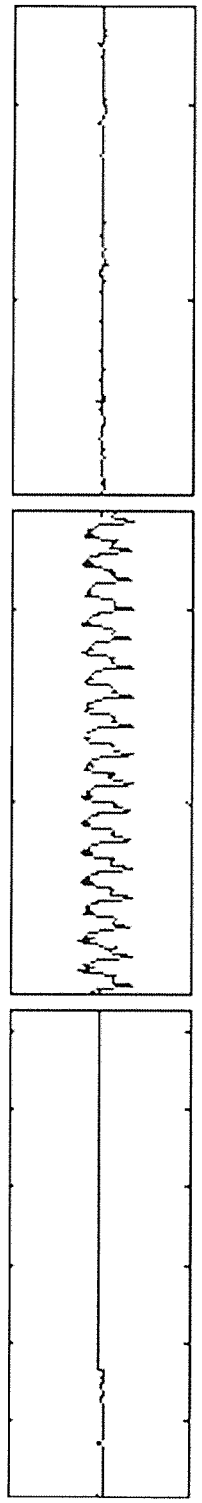
FIG. 11A SAMPLE ECG SIGNAL HAVING NO QRS COMPLEXES AND NO CHEST COMPRESSION ARTIFACTS
FIG. 11B SAMPLE ECG SIGNAL HAVING NO QRS COMPLEXES AND CHEST COMPRESSION ARTIFACTS WITH NO FILTERING
FIG. 11C SAMPLE ECG SIGNAL HAVING NO QRS COMPLEXES AND CHEST COMPRESSION ARTIFACTS WITH FILTER APPLIED

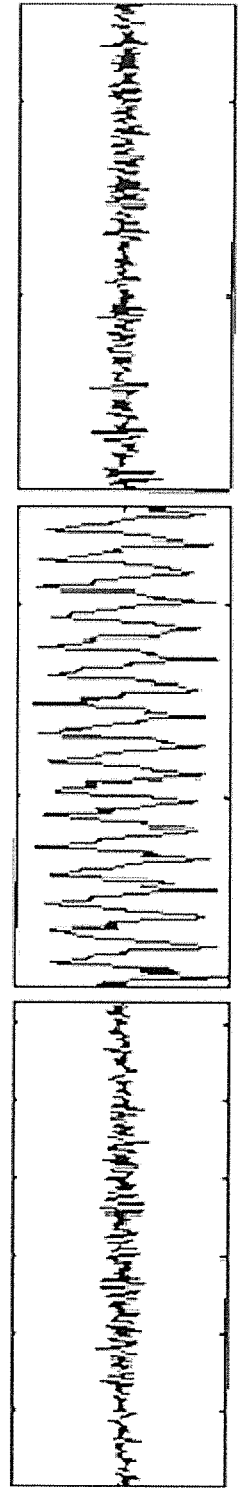
FIG. 12A SAMPLE VF SIGNAL HAVING NO CHEST COMPRESSION ARTIFACTS
FIG. 12B SAMPLE VF SIGNAL HAVING CHEST COMPRESSION ARTIFACTS WITH NO FILTERING
FIG. 12C SAMPLE VF SIGNAL HAVING CHEST COMPRESSION ARTIFACTS WITH FILTER APPLIED

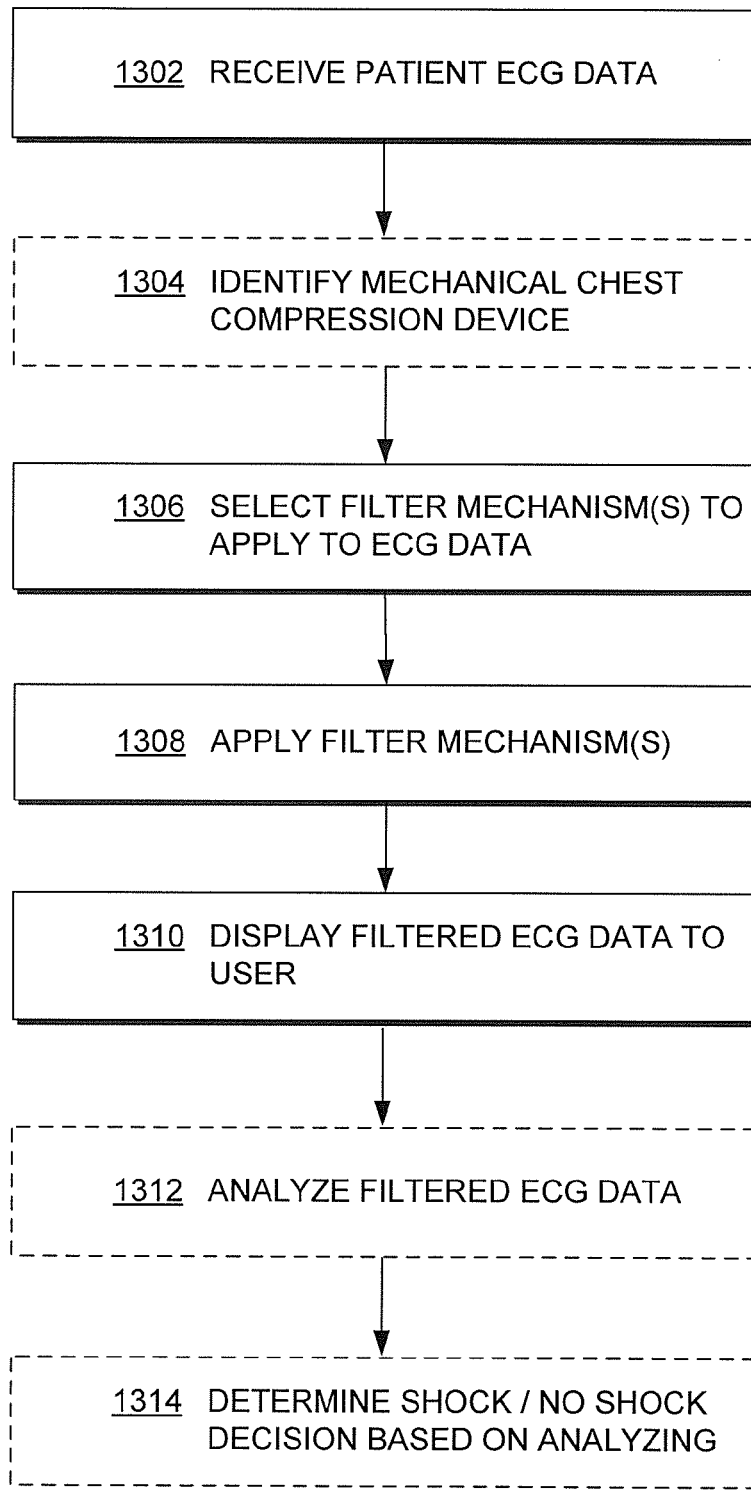
FIG. 13 — METHODS ACCORDING TO EMBODIMENTS

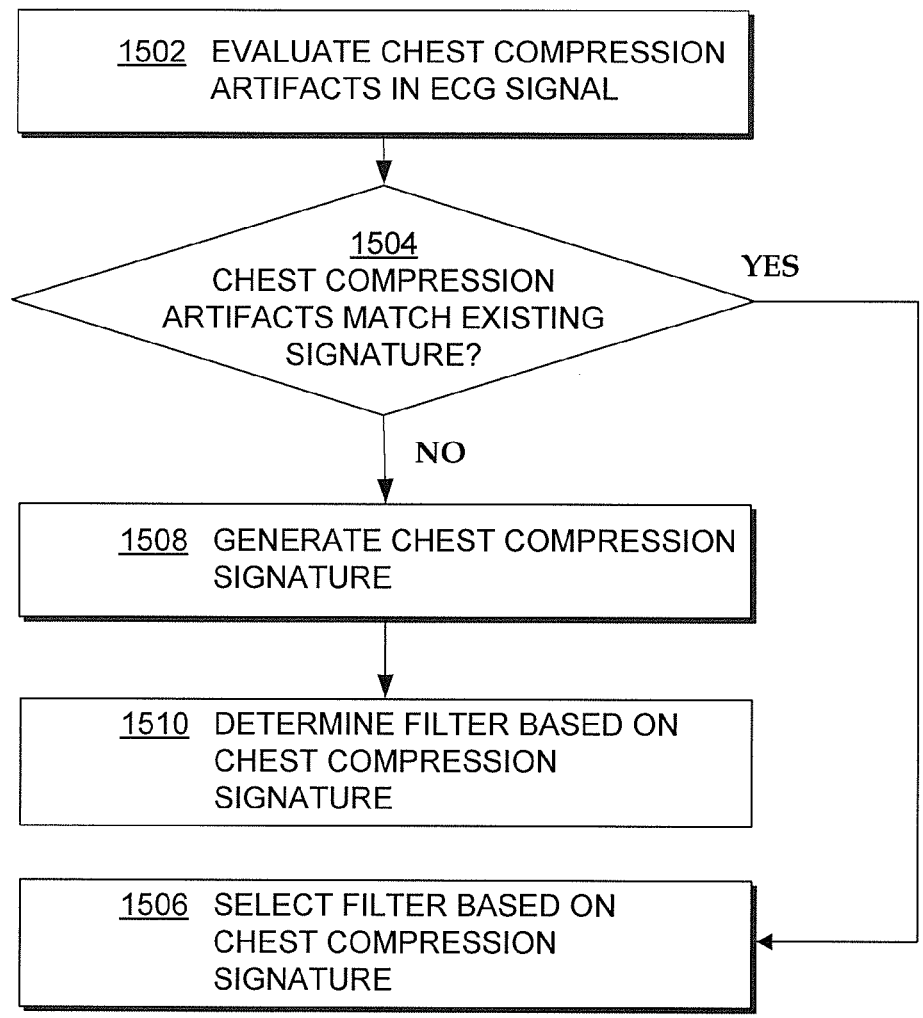
FIG. 15   METHODS ACCORDING TO EMBODIMENTS

FILTER MECHANISM FOR REMOVING ECG ARTIFACT FROM MECHANICAL CHEST COMPRESSIONS

PRIORITY CLAIM

This application claims the benefit of U.S. Provisional Application No. 61/642,407, filed May 3, 2012 and titled Real-Time Filter for Removing ECG Artifact from Mechanical Compression, the content of which is hereby fully incorporated by reference herein.

FIELD

This invention generally relates to medical devices, such as external defibrillators.

BACKGROUND

In humans, the heart beats to sustain life. In normal operation, it pumps blood through the various parts of the body. More particularly, the various chamber of the heart contract and expand in a periodic and coordinated fashion, which causes the blood to be pumped regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle, then, expels the blood, forcing it to circulate to the various parts of the body.

The heart chambers pump because of the heart's electrical control system. More particularly, the sinoatrial (SA) node generates an electrical impulse, which generates further electrical signals. These further signals cause the above-described contractions of the various chambers in the heart, in the correct sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia. Arrhythmias may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In a SCA, the heart fails to pump blood effectively, and, if not treated, death can occur. In fact, it is estimated that SCA results in more than 250,000 deaths per year in the United States alone. Further, a SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood to deliver enough oxygen to the vital organs. The person's condition will deteriorate rapidly and, if not reversed in time, they will die soon, e.g. within ten minutes.

Ventricular Fibrillation can often be reversed using a lifesaving device called a defibrillator. A defibrillator, if applied properly, can administer an electrical shock to the heart. The shock may terminate the VF, thus giving the heart the opportunity to resume pumping blood. If VF is not terminated, the shock may be repeated, often at escalating energies.

A challenge with defibrillation is that the electrical shock must be administered very soon after the onset of VF. There is not much time: the survival rate of persons suffering from VF decreases by about 10% for each minute the administration of a defibrillation shock is delayed. After about 10 minutes the rate of survival for SCA victims averages less than 2%.

The challenge of defibrillating early after the onset of VF is being met in a number of ways. First, for some people who are considered to be at a higher risk of VF or other heart arrhythmias, an Implantable Cardioverter Defibrillator (ICD) can be implanted surgically. An ICD can monitor the person's heart, and administer an electrical shock as needed. As such, an ICD reduces the need to have the higher-risk person be monitored constantly by medical personnel.

Regardless, VF can occur unpredictably, even to a person who is not considered at risk. As such, VF can be experienced by many people who lack the benefit of ICD therapy. When VF occurs to a person who does not have an ICD, they collapse, because blood flow has stopped. They should receive therapy quickly.

For a VF victim without an ICD, a different type of defibrillator can be used, which is called an external defibrillator. External defibrillators have been made portable, so they can be brought to a potential VF victim quickly enough to revive them.

During VF, the person's condition deteriorates, because the blood is not flowing to the brain, heart, lungs, and other organs. Blood flow must be restored, if resuscitation attempts are to be successful.

Cardiopulmonary Resuscitation (CPR) is one method of forcing blood flow in a person experiencing cardiac arrest. In addition, CPR is the primary recommended treatment for some patients with some kinds of non-VF cardiac arrest, such as asystole and pulseless electrical activity (PEA). CPR is a combination of techniques that include chest compressions to force blood circulation, and rescue breathing to force respiration.

Properly administered CPR provides oxygenated blood to critical organs of a person in cardiac arrest, thereby minimizing the deterioration that would otherwise occur. As such, CPR can be beneficial for persons experiencing VF, because it slows the deterioration that would otherwise occur while a defibrillator is being retrieved. Indeed, for patients with an extended down-time, survival rates are higher if CPR is administered prior to defibrillation.

Advanced medical devices can actually coach a rescuer who performs CPR. For example, a medical device can issue instructions, and even prompts, for the rescuer to perform CPR more effectively.

BRIEF SUMMARY

The present description gives instances of devices, systems, software and methods, the use of which may help overcome problems and limitations of the prior art.

In certain embodiments, an external medical device may include a housing, an energy storage module within the housing for storing an electrical charge, and a defibrillation port for guiding via electrodes the stored electrical charge to a person. The device may also include a processor in the housing configured to receive a signal from a patient receiving chest compressions and apply at least one filter to remove from the signal chest compression artifacts resulting from the chest compressions being delivered to the patient.

An advantage over the prior art is that an external medical device in accordance with the disclosed technology can present to a user a cleaner signal than would otherwise be provided in situations where a patient is receiving chest compressions. Also, the device may determine from chest compression artifacts in the patient signal a chest compression signature that corresponds to at least one particular type of chest compression device.

These and other features and advantages of this description will become more readily apparent from the following Detailed Description, which proceeds with reference to the drawings, in which:

BRIEF DESCRIPTION OF THE DRAWINGS

FIG. 1 is a diagram of a scene where an external defibrillator is used to save the life of a person according to embodiments.

FIG. 2 is a table listing two main types of the external defibrillator shown in FIG. 1, and who they might be used by.

FIG. 11A is a time diagram of an ECG signal having no QRS complexes and no chest compression artifacts.

FIG. 11B is a time diagram of an ECG signal having no QRS complexes and chest compression artifacts with no filtering.

FIG. 11C is a time diagram of an ECG signal having no QRS complexes and chest compression artifacts with a filter mechanism applied thereto.

FIG. 12A is a time diagram of a VF signal having no chest compression artifacts.

FIG. 12B is a time diagram of a VF signal having chest compression artifacts with no filtering.

FIG. 12C is a time diagram of a VF signal having chest compression artifacts with a filter mechanism applied thereto.

FIG. 13 is a flowchart for illustrating methods according to embodiments.

FIG. 15 is a flowchart for illustrating other methods according to embodiments.

DETAILED DESCRIPTION

Figure 3:
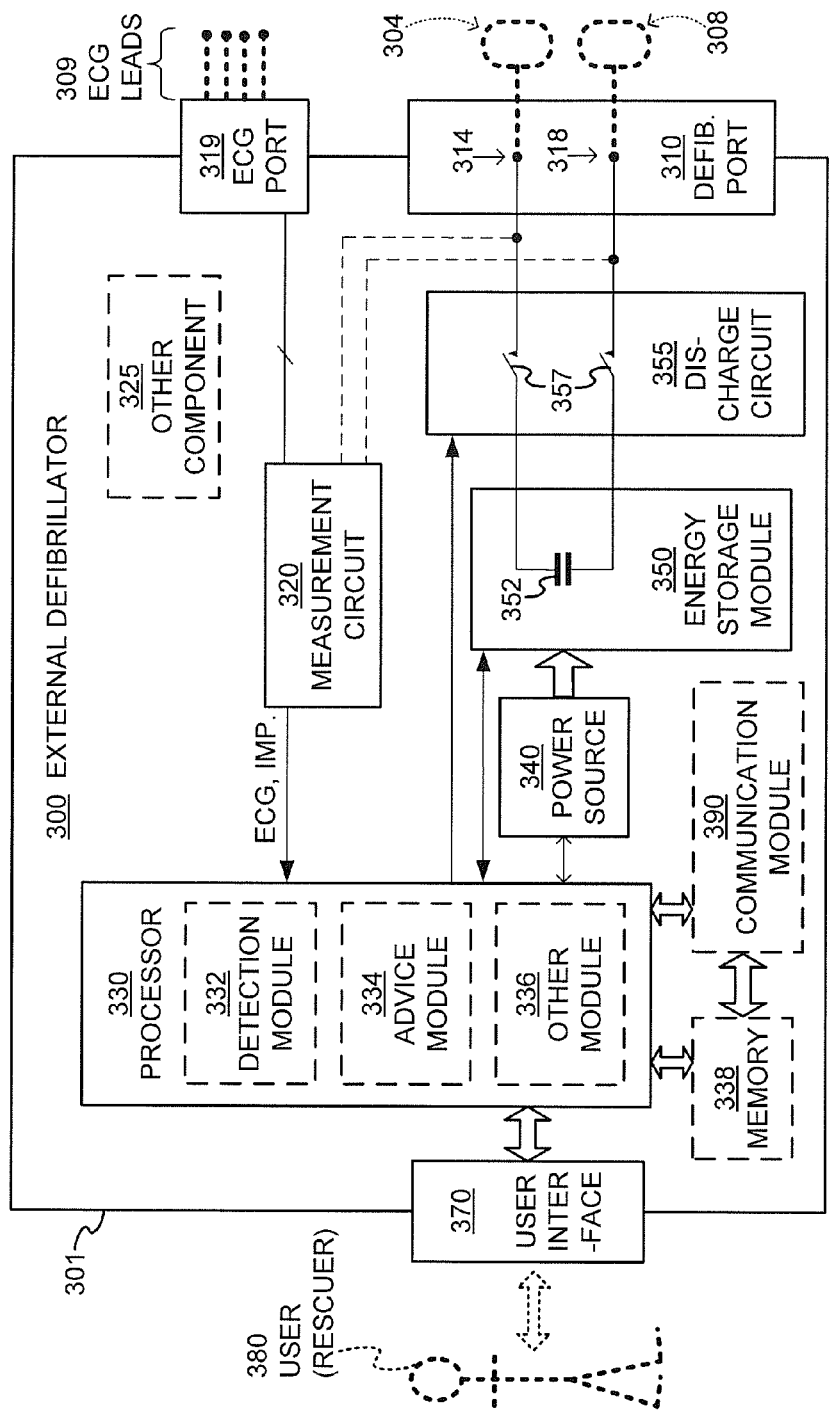
FIG. 3 is a functional block diagram showing components of an external defibrillator, such as the one shown in FIG. 1, which is made according to embodiments.

As has been mentioned, the present description is about medical devices, methods of operating such medical devices, and a programmed processor to control such medical devices for removing chest compression artifacts from an ECG signal for a patient receiving chest compressions.

Embodiments are now described in more detail.

FIG. 1 is a diagram of a defibrillation scene. A person 82 is lying on their back. Person 82 could be a patient in a hospital, or someone found unconscious, and then turned to be on their back. Person 82 is experiencing a condition in their heart 85, which could be Ventricular Fibrillation (VF).

A portable external defibrillator 100 has been brought close to person 82. At least two defibrillation electrodes 104, 108 are usually provided with external defibrillator 100, and are sometimes called electrodes 104, 108. Electrodes 104, 108 are coupled with external defibrillator 100 via respective electrode leads 105, 109. A rescuer (not shown) has attached electrodes 104, 108 to the skin of person 82.

Defibrillator 100 is administering, via electrodes 104, 108, a brief, strong electric pulse 111 through the body of person 82. Pulse 111, also known as a defibrillation shock, goes also through heart 85, in an attempt to restart it, for saving the life of person 82.

Defibrillator 100 can be one of different types, each with different sets of features and capabilities. The set of capabilities of defibrillator 100 is determined by planning who would use it, and what training they would be likely to have. Examples are now described.

FIG. 2 is a table listing two main types of external defibrillators, and who they are primarily intended to be used by. A first type of defibrillator 100 is generally called a defibrillator-monitor, because it is typically formed as a single unit in combination with a patient monitor. A defibrillator-monitor is sometimes called monitor-defibrillator. A defibrillator-monitor is intended to be used by persons in the medical professions, such as doctors, nurses, paramedics, emergency medical technicians, etc. Such a defibrillator-monitor is intended to be used in a pre-hospital or hospital scenario.

As a defibrillator, the device can be one of different varieties, or even versatile enough to be able to switch among different modes that individually correspond to the varieties. One variety is that of an automated defibrillator, which can determine whether a shock is needed and, if so, charge to a predetermined energy level and instruct the user to administer the shock. Another variety is that of a manual defibrillator, where the user determines the need and controls administering the shock.

As a patient monitor, the device has features additional to what is minimally needed for mere operation as a defibrillator. These features can be for monitoring physiological indicators of a person in an emergency scenario. These physiological indicators are typically monitored as signals. For example, these signals can include a person's full ECG (electrocardiogram) signals, or impedance between two electrodes.

Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on. These signals can be further stored and/or transmitted as patient data.

A second type of external defibrillator 100 is generally called an AED, which stands for "Automated External Defibrillator". An AED typically makes the shock/no shock determination by itself, automatically. Indeed, it can sense enough physiological conditions of the person 82 via only the shown defibrillation electrodes 104, 108 of FIG. 1. In its present embodiments, an AED can either administer the shock automatically, or instruct the user to do so, e.g. by pushing a button. Being of a much simpler construction, an AED typically costs much less than a defibrillator-monitor. As such, it makes sense for a hospital, for example, to deploy AEDs at its various floors, in case the more expensive defibrillator-monitor is more critically being deployed at an Intensive Care Unit, and so on.

AEDs, however, can also be used by people who are not in the medical profession. More particularly, an AED can be used by many professional first responders, such as policemen, firemen, etc. Even a person with only first-aid training can use one. And AEDs increasingly can supply instructions to whoever is using them.

AEDs are thus particularly useful, because it is so critical to respond quickly, when a person suffers from VF. Indeed, the people who will first reach the VF sufferer may not be in the medical professions.

Increasing awareness has resulted in AEDs being deployed in public or semi-public spaces, so that even a member of the public can use one, if they have obtained first aid and CPR/AED training on their own initiative. This way, defibrillation can be administered soon enough after the onset of VF, to hopefully be effective in rescuing the person.

There are additional types of external defibrillators, which are not listed in FIG. 2. For example, a hybrid defibrillator can have aspects of an AED, and also of a defibrillator-monitor. A usual such aspect is additional ECG monitoring capability.

FIG. 3 is a diagram showing components of an external defibrillator 300 made according to embodiments. These components can be, for example, in external defibrillator 100 of FIG. 1. Plus, these components of FIG. 3 can be provided in a housing 301, which is also known as casing 301.

External defibrillator 300 is intended for use by a user 380, who would be the rescuer. Defibrillator 300 typically includes a defibrillation port 310, such as a socket in housing 301. Defibrillation port 310 includes nodes 314, 318. Defibrillation electrodes 304, 308, which can be similar to electrodes 104, 108, can be plugged in defibrillation port 310, so as to make electrical contact with nodes 314, 318, respectively. It is also possible that electrodes can be connected continuously to defibrillation port 310, etc. Either way, defibrillation port 310 can be used for guiding via electrodes to person 82 an electrical charge that has been stored in defibrillator 300, as will be seen later in this document.

If defibrillator 300 is actually a defibrillator-monitor, as was described with reference to FIG. 2, then it will typically also have an ECG port 319 in housing 301, for plugging in ECG leads 309. ECG leads 309 can help sense an ECG signal, e.g. a 12-lead signal, or from a different number of leads. Moreover, a defibrillator-monitor could have additional ports (not shown), and an other component 325 structured to filter the ECG signal, e.g., apply at least one filter to the signal so as to remove chest compression artifacts resulting from chest compressions being delivered to the person 82.

Defibrillator 300 also includes a measurement circuit 320. Measurement circuit 320 receives physiological signals from ECG port 319, and also from other ports, if provided. These physiological signals are sensed, and information about them is rendered by circuit 320 as data, or other signals, etc.

If defibrillator 300 is actually an AED, it may lack ECG port 319. Measurement circuit 320 can obtain physiological signals through nodes 314, 318 instead, when defibrillation electrodes 304, 308 are attached to person 82. In these cases, a person's ECG signal can be sensed as a voltage difference between electrodes 304, 308. Plus, impedance between electrodes 304, 308 can be sensed for detecting, among other things, whether these electrodes 304, 308 have been inadvertently disconnected from the person.

Defibrillator 300 also includes a processor 330. Processor 330 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 can be considered to have a number of modules. One such module can be a detection module 332, which senses outputs of measurement circuit 320. Detection module 332 can include a VF detector. Thus, the person's sensed ECG can be used to determine whether the person is experiencing VF.

Another such module in processor 330 can be an advice module 334, which arrives at advice based on outputs of detection module 332. Advice module 334 can include a Shock Advisory Algorithm, implement decision rules, and so on. The advice can be to shock, to not shock, to administer other forms of therapy, and so on. If the advice is to shock, some external defibrillator embodiments merely report that to the user, and prompt them to do it. Other embodiments further execute the advice, by administering the shock. If the advice is to administer CPR, defibrillator 300 may further issue prompts for it, and so on.

Processor 330 can include additional modules, such as module 336, for other functions. In addition, if other component 325 is indeed provided, it may be operated in part by processor 330, etc.

Defibrillator 300 optionally further includes a memory 338, which can work together with processor 330. Memory 338 may be implemented in any number of ways. Such ways include, by way of example and not of limitation, nonvolatile memories (NVM), read-only memories (ROM), random access memories (RAM), any combination of these, and so on. Memory 338, if provided, can include programs for processor 330, and so on. The programs can be operational for the inherent needs of processor 330, and can also include protocols and ways that decisions can be made by advice module 334. In addition, memory 338 can store prompts for user 380, etc. Moreover, memory 338 can store patient data.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include AC power override, for where AC power will be available, and so on. In some embodiments, power source 340 is controlled by processor 330.

Defibrillator 300 additionally includes an energy storage module 350. Module 350 is where some electrical energy is stored, when preparing it for sudden discharge to administer a shock. Module 350 can be charged from power source 340 to the right amount of energy, as controlled by processor 330. In typical implementations, module 350 includes one or more capacitors 352, and so on.

Defibrillator 300 moreover includes a discharge circuit 355. Circuit 355 can be controlled to permit the energy stored in module 350 to be discharged to nodes 314, 318, and thus also to defibrillation electrodes 304, 308. Circuit 355 can include one or more switches 357. Those can be made in a number of ways, such as by an H-bridge, and so on.

Defibrillator 300 further includes a user interface 370 for user 380. User interface 370 can be made in any number of ways. For example, interface 370 may include a screen, to display what is detected and measured, provide visual feedback to the rescuer for their resuscitation attempts, and so on. Interface 370 may also include a speaker, to issue voice prompts, etc. Interface 370 may additionally include various controls, such as pushbuttons, keyboards, and so on. In addition, discharge circuit 355 can be controlled by processor 330, or directly by user 380 via user interface 370, and so on.

Defibrillator 300 can optionally include other components. For example, a communication module 390 may be provided for communicating with other machines. Such communication can be performed wirelessly, or via wire, or by infrared communication, and so on. This way, data can be communicated, such as patient data, incident information, therapy attempted, CPR performance, and so on. A feature of a defibrillator can be CPR-prompting. Prompts are issued to the user, visual or by sound, so that the user can administer CPR. Examples are taught in U.S. Pat. Nos. 6,334,070 and 6,356,785.

Figure 4:
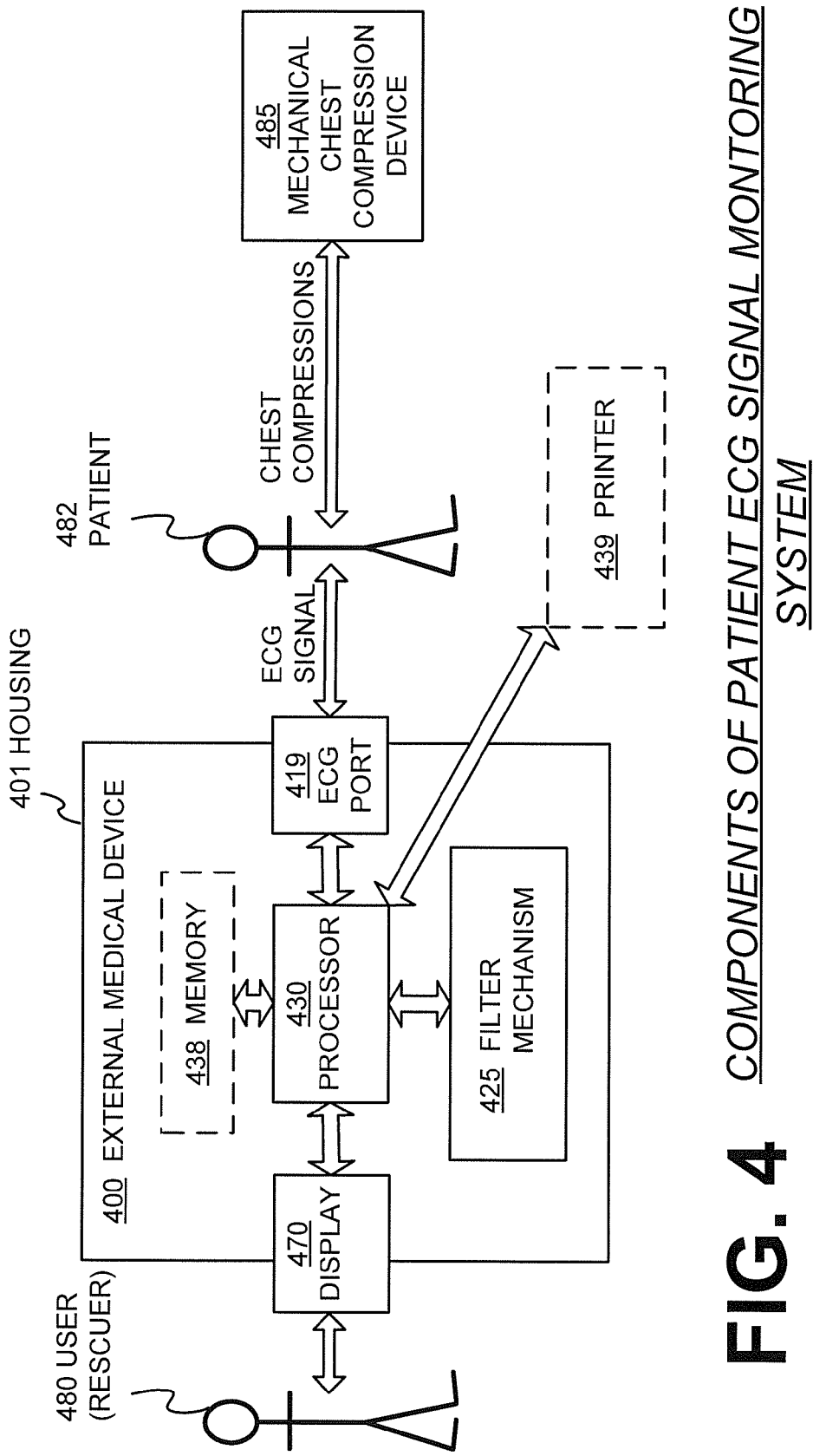
FIG. 4 is a functional block diagram showing components of a patient ECG signal monitoring system according to embodiments.

FIG. 4 is a functional block diagram showing components of a patient ECG signal monitoring system according to embodiments. The system includes an external medical device 400, such as an external defibrillator, having a housing 401, a display 470 in connection with the housing 401, and a processor 430 within the housing 401. One having ordinary skill in the art will recognize that systems according to embodiments generally require no additional sensors or sensor mechanisms than those already provided.

In the example, the system also includes a mechanical chest compression device 485. The mechanical chest compression device 485 may deliver compressions at 100+/−0.01 compressions/minute, which is 1⅔+/−0.00017 Hz. Such precise frequency control is unusual for typical chest compression devices. An ECG signal may thus be corrupted by chest compression artifacts corresponding to chest compressions delivered by the chest compression device 485 to the patient 482. Such artifacts may have an artifact fundamental frequency of 1⅔ Hz, and the artifact signal may also contain harmonics of 1⅔ Hz, which will show up at multiples of 1⅔ Hz, e.g., 3⅓ Hz, 5.0 Hz, and 6⅔ Hz. The spectral content of these frequency components is generally extremely narrow.

The processor 430 may be configured to receive an input signal containing ECG data for a patient 482 receiving chest compressions from the mechanical chest compression device 485. The input signal may be received via an ECG port 419 in connection with the housing 401. In certain embodiments, the processor 430 is further configured to detect the chest compressions being delivered to the patient 482.

The processor 430 may be further configured to select at least one filter mechanism 425, the mechanical chest compression device 485 having a chest compression frequency f. The mechanical chest compression device 485 may provide an indication of the frequency f to the processor 430.

In certain embodiments, the at least one filter mechanism 425 comprises a comb filter. The comb filter may be non-adaptive. In other embodiments, the at least one filter mechanism 425 comprises a plurality of notch filters. Each of the notch filters may be non-adaptive. One having ordinary skill in the art will readily recognize that various other filter mechanisms may be used in addition to or in place of a comb filter or notch filters.

Certain conventional CPR artifact filters may be adaptive in nature. As used herein, an adaptive filter generally refers to a filter whose transfer function is dependent on the input signal. An adaptive filter may adjust its filter coefficients, center frequency, rolloff, notch width, Q, or other characteristic based on the input signal. Non-adaptive filters according to embodiments generally use predetermined coefficients that may precisely set the transfer function independent of the input signal.

It is possible that a device incorporating this invention may include multiple non-adaptive filters. The appropriate filter may be selected based on input signal characteristics, such as the frequency content of the ECG signal or impedance signal. Alternatively, the appropriate filter may be selected by communication with the mechanical chest compression device, or through a user input selection.

In certain embodiments, the selecting of the at least one filter mechanism 425 is performed responsive to an identification of the mechanical chest compression device 485 being used to deliver the chest compressions to the patient 482. Alternatively or in addition thereto, the processor 430 may be configured to select the at least one filter mechanism 425 responsive to input received from the mechanical chest compression device 485 delivering the chest compressions to the patient 482. In certain embodiments, the processor 430 may be configured to select the at least one filter mechanism 425 responsive to input received from a user 480.

The processor 430 may be configured to apply the at least one filter mechanism 425 to the ECG data to at least substantially remove chest compression artifacts from the ECG data, wherein the chest compression artifacts correspond to the chest compressions being delivered to the patient 482 by the mechanical chest compression device 485, and wherein the at least one filter mechanism 425 substantially rejects content in the frequency f plus content in at least one more frequency that is a higher harmonic to the frequency f. In certain embodiments, application of the at least one filter mechanism 425 to the ECG data reduces an amplitude of the chest compression artifacts by at least 20 dB relative to the input signal.

The processor 430 may be further configured to cause the display 470 to visually present the filtered ECG data to the user 480. Alternatively or in addition thereto, the processor 430 may be configured to cause an optional printer 439 to print out the filtered ECG data. In certain embodiments, the processor 430 may cause the filtered ECG to be stored, e.g., by a memory 438, for later review or downloading to a post-event review tool.

In certain embodiments, the processor 430 is preconfigured to apply the at least one filter mechanism 425. In other embodiments, the processor 430 may be configured to apply the at least one filter mechanism 425 to the ECG data responsive to input received from the user 480.

In certain embodiments, the ECG data is received in real-time. In other embodiments, the ECG data is received in a post-event review. In these embodiments, the ECG data may have been recorded from defibrillation patches or an ECG monitor having multiple leads, e.g., three or more leads. The at least one filter mechanism 425 may be applied to the ECG data regardless of whether the device that recorded the signal even had the at least one filter mechanism 425. Indeed, the ECG data could be provided, e.g., sent via e-mail, to another user who causes the at least one filter mechanism 425 to be applied thereto. Post-event filtering may be used for establishing the time of re-fibrillation or examining the signal characteristics prior to fibrillation, for example.

For a patient experiencing VF, VF quality measures such as median VF frequency, AMSA, and the scaling exponent may be used for deciding when to apply chest compressions to the patient 482 and when to defibrillate the patient 482. By applying the at least one filter mechanism 425, these parameters may be accurately measured during CPR.

The processor 430 may be configured to determine a pattern of the chest compression artifacts corresponding to the chest compressions being delivered to the patient 482. The pattern may be based on starting and stopping of the chest compressions being delivered to the patient 482, for example. The processor 430 may be configured to determine whether a chest compression artifact pattern matches an existing chest compression signature. In certain embodiments, the processor 430 may be further configured to merge information corresponding to the pattern with information corresponding to the predetermined pattern responsive to a determination that the pattern matches the existing chest compression signature. In other embodiments, the processor 430 may be configured to generate a new chest compression signature responsive to a determination that the pattern does not match the existing chest compression signature.

In certain embodiments, the processor 430 is configured to suppress application of the at least one filter mechanism 425 to the ECG data responsive to a determination that the mechanical chest compression device 485 is no longer delivering chest compressions to the patient 482. The processor 430 may be further configured to resume application of the at least one filter mechanism 425 to the ECG data responsive to a determination that the mechanical chest compression device 485 has resumed delivery of chest compressions to the patient 482. The presence and/or absence of chest compressions may be detected using a measurement of the impedance signal. For example, the RMS value of a one-second window of the impedance signal is generally a reliable indicator of chest compressions.

In certain embodiments, the processor 430 is configured to generate a report, e.g., CPR statistics, corresponding to the chest compressions that were delivered to the patient 482. Alternatively or in addition thereto, the processor 430 may be configured to generate a report corresponding to the mechanical chest compression device 485 that was used to deliver the chest compressions to the patient 482.

In certain embodiments, the processor 430 is further configured to monitor an impedance signal corresponding to the patient. An impedance waveform could be filtered to remove compression artifacts, for example, to allow for detection of ventilation artifacts or the presence of cardiac output. The processor 430 may be further configured to detect return of spontaneous circulation (ROSC) by applying a signal-averaging filter to the impedance signal, e.g., combining a comb filter with the signal-averaging filter.

In certain embodiments, the processor 430 is further configured to analyze the filtered ECG data. In these embodiments, the processor 430 may be further configured to determine a shock/no shock decision based on the analysis of the filtered ECG data.

In certain embodiments, the chest compressions are manually delivered to the patient 482 by the rescuer 480. In these embodiments, the rescuer 480 may use a metronome while delivering the chest compressions to the patient 482 in order to deliver compressions at a very precise rate, for example. The processor 430 may be configured to select the at least one filter mechanism 425 based at least in part on a chest compression rate corresponding to the chest compressions being delivered to the patient 482. These embodiments may further include informing the rescuer 480 whether the CPR is currently effective, i.e., the chest compressions are being administered at the correct rate. The rescuer 480 may thus judge whether to trust the filtered display 470.

In certain embodiments, the device 400 further includes an energy storage module within the housing 401 for storing an electrical charge and a defibrillation port for guiding via electrodes the stored electrical charge to the patient 482.

Figure 5:
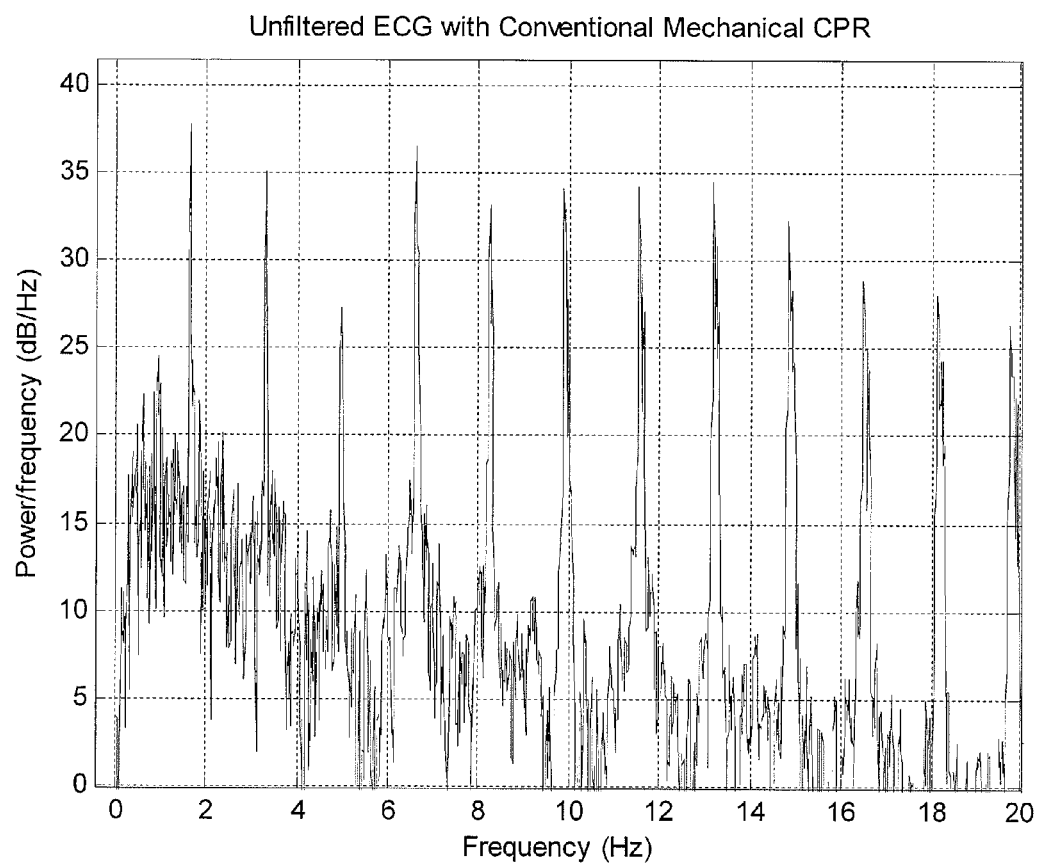
FIG. 5 is a graphical illustration of a fast Fourier transform of an ECG signal of an asystolic patient receiving chest compressions from a conventional mechanical chest compression device.

FIG. 5 is a graphical illustration of a fast Fourier transform of an ECG signal of an asystolic patient, such as patient 482 of FIG. 4, receiving chest compressions from a conventional mechanical chest compression device. As can be seen from the illustrated example, the ECG signal from an asystolic patient generally contains only artifacts because the patient has no active cardiac signal. Multiple spectral peaks are evident, with the fundamental frequency of the chest compressions appearing at 1.6 Hz and other peaks representing harmonic frequencies. The width of these spectral peaks varies from approximately 0.15 Hz at the fundamental frequency up to approximately 0.5 Hz for the $6^{th}$ harmonic (10 Hz). It would be difficult to remove the CPR artifact from the illustrated signal due to the requirement for a relatively wide filter, which would necessarily remove much of the cardiac signal, thus causing distortion that would adversely impact the signal.

Signals corresponding to conventional mechanical CPR devices generally have only broad spectral peaks, and the locations of such peaks are typically not precisely controlled. The fundamental frequency may vary from one device to another, or from one application to another. For example, the fundamental frequency may vary from 1.4 Hz to 1.7 Hz. Such variation generally prevents application of a non-adaptive filter, e.g., a comb filter, with a narrow stop band.

Conventional CPR artifact filters have been unsuccessful at removing CPR artifacts, in part, because they typically focus on removing the fundamental frequency while paying little, if any, attention to the harmonic frequencies. In the example illustrated by FIG. 5, the $12^{th}$ harmonic is only about 11 dB down from the fundamental frequency. In order to produce a clean ECG signal, CPR artifacts usually need to be attenuated by at least 20 dB, and possibly as much as 40 dB. In order to clean up the signal, frequencies up to at least the $12^{th}$ harmonic must typically be removed.

Figure 6:
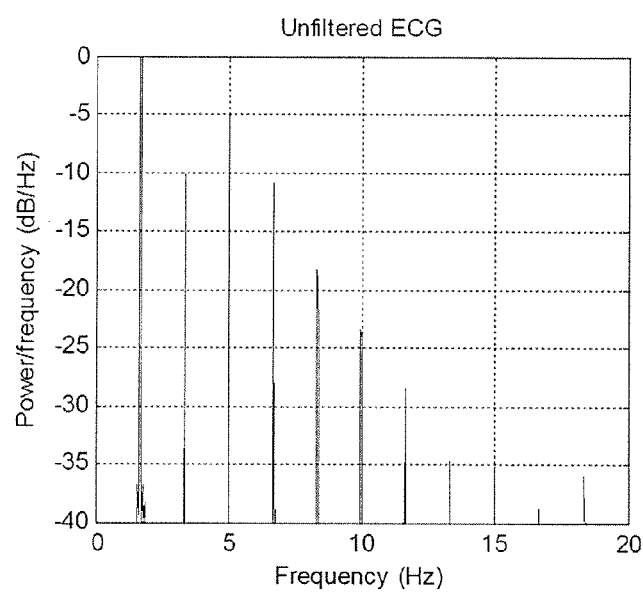
FIG. 6 is a graphical illustration of a fast Fourier transform of an ECG signal from an asystolic patient receiving chest compressions from a mechanical chest compression device having precise frequency control according to embodiments.

FIG. 6 is a graphical illustration of a fast Fourier transform of an ECG signal from an asystolic patient, such as the patient 482 of FIG. 4, receiving chest compressions from a mechanical chest compression device having precise frequency control according to embodiments. The spectral peaks of the artifacts generated by this device are typically very narrow, e.g., less than 0.1 Hz wide. This narrow spectral content enables the cardiac ECG signal to be separated from chest compression artifact. As with the signal of FIG. 5, multiple frequency harmonics are present in the signal of FIG. 6, in which the $5^{th}$ harmonic is less than 20 dB down and the $11^{th}$ harmonic is less than 40 dB down. In order to clean up the signal, harmonics up to at least the $5^{th}$ harmonic, and possibly as high as the $11^{th}$ harmonic, should be removed.

Figure 7:
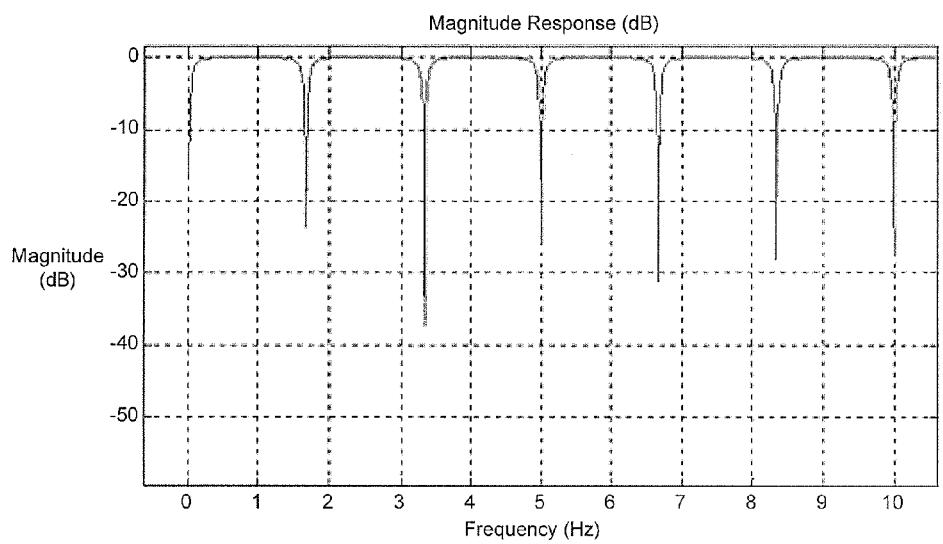
FIG. 7 is a graphical illustration of the frequency response of a comb filter suitable for removing chest compression artifacts from an ECG signal according to embodiments.

FIG. 7 is a graphical illustration of the frequency response of a comb filter, such as a high-Q comb filter, e.g., Q=16, suitable for removing chest compression artifacts from an ECG signal according to embodiments. A comb filter intrinsically removes the fundamental frequency and all of the harmonics. If the Q is set relatively high, e.g. 16, the filter will surgically remove the artifact frequencies and leave the other frequencies relatively untouched.

In general, high-Q filters are more frequency-selective than low-Q filters. For example, a comb filter having Q=16 will generally have a 3 dB notch width of about 0.1 Hz, whereas a comb filter having Q=4 will typically have a 3 dB notch width of about 0.5 Hz. A filter having Q=2 has approximately a 3 dB notch width of about 1 Hz and usually removes almost as much of the signal as it retains. A lower-Q filter will generally remove more artifacts from a signal than a high-Q filter but will also remove more of the signal itself. In addition, a low-Q filter tends to produce more ringing, which often provides additional distortion.

In order to effectively remove CPR artifacts resulting from application of a conventional chest compression device, a very low-Q filter is preferable. Assuming that at least 20 dB of attenuation is needed, even a filter having Q=2 would generally not be effective in removing the artifact from the signal due to the spectral peaks of the artifact being too tall and too broad.

Because the spectral content of a mechanical CPR device according to embodiments is generally extremely narrow, a high-Q filter may be used to remove the compression artifact and retain the cardiac ECG signal with little distortion. Because a mechanical CPR device according to embodiments generally produces compressions at a precisely known frequency, the artifact may be filtered using a non-adaptive filter. Combining these two aspects (narrow frequency content and precise frequency control) according to embodiments may thus enable a high-Q comb filter to be used as an effective filter for removing CPR artifacts from the input signal.

The following is a Z transform of a suitable comb filter:

$$H(z) = \frac{a(z^{-1} - z^{-n})}{1 - bz^{-n}}$$

where "a" is a gain constant, "b" sets the filter Q, and "n" is an integer that sets the notch frequencies. The Q of this filter may be set by a single coefficient, the constant "b." For example, b=0.82 for a Q of 16. The value of "n" and the sample frequency may be set to locations of the comb notch frequencies. In situations where n=75 and the sample rate is 125 Hz, for example, the notch frequencies would be 1⅔ Hz, 3⅓ Hz, 5.0 Hz, etc.

A comb filter generally introduces very little signal delay. The signal is typically delayed only one sample, which is 8 milliseconds at 125 Hz, for example. From a user's standpoint, this delay is imperceptible. This is in contrast to certain filter structures, such as finite impulse response (FIR) filters, that can delay the signal by a second or more. Such delay could lead to a misalignment between the filtered ECG and other signals, such as the unfiltered ECG or an invasive blood pressure waveform, that could be confusing to the user. Alternatively or in addition thereto, a collection of narrow notch filters, e.g., one filter for the fundamental frequency and one for every harmonic that needs to be removed, may be used. This small delay may make a comb filter particularly suitable for an ECG display, in which signal delays or misalignment with other monitoring parameters may be objectionable.

Figure 8:
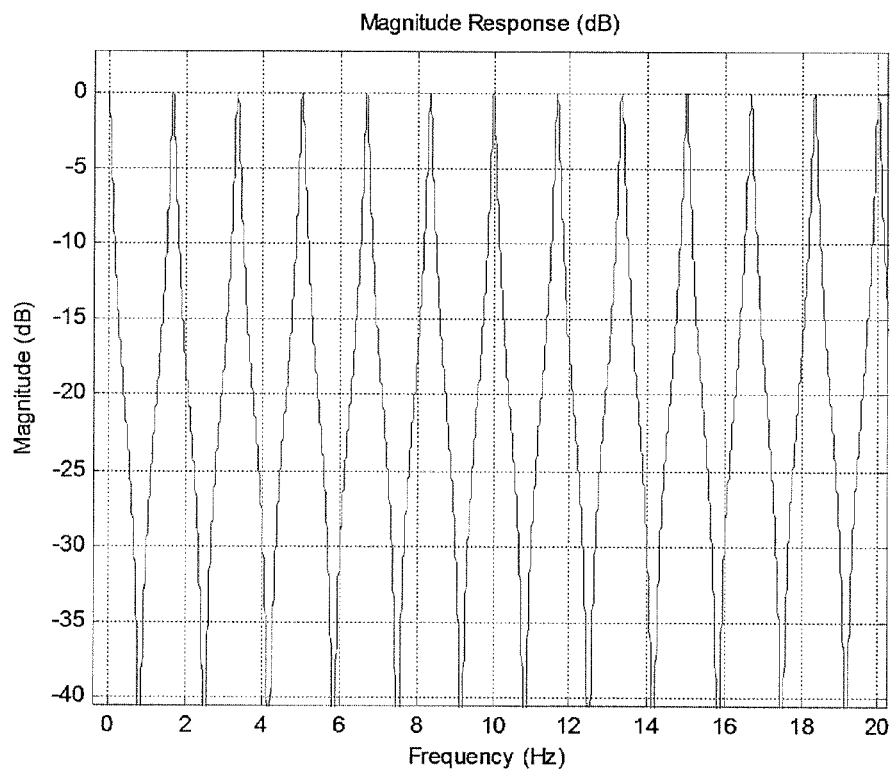
FIG. 8 is a graphical illustration of the frequency response of an inverse comb filter suitable for removing chest compression artifacts from an ECG signal according to embodiments.

FIG. 8 is a graphical illustration of the frequency response of an inverse comb filter suitable for detecting chest compression artifacts from an ECG signal according to embodiments. An inverse comb filter is generally similar to a comb filter except that it passes the comb frequencies instead of rejecting them. Such an inverse comb filter may be particularly suitable for detection of mechanical compressions delivered at certain rates, e.g., 100 compressions/minute.

Figure 9:
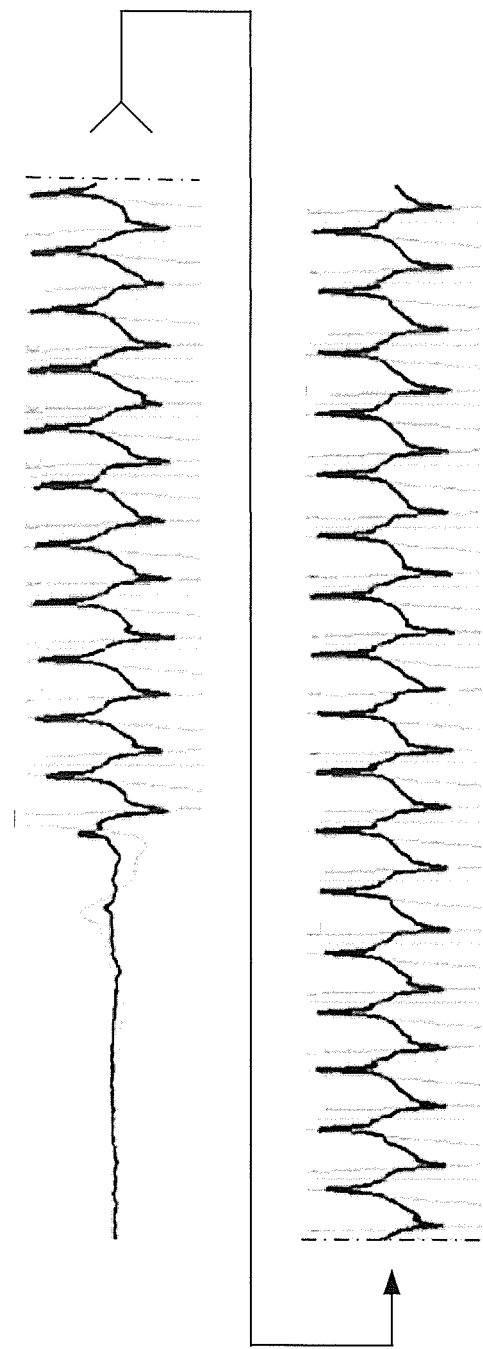
FIG. 9 is a time diagram of patient ECG data in the form of signals.

FIG. 9 is a time diagram of patient ECG data in the form of signals. The ECG data in this example is presently exhibiting an impulsive waveform having signal spikes or peaks that include both positive peaks and negative peaks. For example, the ECG data of FIG. 9 may generally correspond to a patient, such as the patient 482 of FIG. 4, that is neither experiencing a cardiac event nor receiving chest compressions, e.g., from a chest compression device such as the mechanical chest compression device 485 of FIG. 4.

Figures 10A, 10B, 10C:
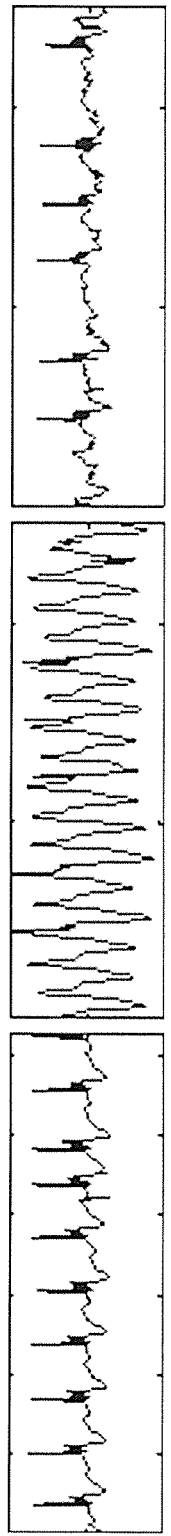
FIG. 10A is a time diagram of an ECG signal having QRS complexes and no chest compression artifacts.
FIG. 10B is a time diagram of an ECG signal having QRS complexes and chest compression artifacts with no filtering.
FIG. 10C is a time diagram of an ECG signal having QRS complexes and chest compression artifacts with a filter mechanism applied thereto.

FIG. 10A is a time diagram of an ECG signal having QRS complexes and no chest compression artifacts. The QRS complexes generally include both positive peaks and negative peaks. As with the ECG data of FIG. 9, the ECG signal of FIG. 10A may generally correspond to a patient, such as the patient 482 of FIG. 4, that is neither experiencing a cardiac event nor receiving chest compressions, e.g., from a chest compression device such as the mechanical chest compression device 485 of FIG. 4.

FIG. 10B is a time diagram of an ECG signal having QRS complexes and chest compression artifacts with no filtering. For example, the ECG signal of FIG. 10B may generally correspond to a patient, such as the patient 482 of FIG. 4, that is not necessarily experiencing a cardiac event but is presently receiving chest compressions, e.g., from a chest compression device such as the mechanical chest compression device 485 of FIG. 4. As can be readily ascertained by even a causal viewer, the QRS complexes in the ECG signal are at least partially, if not fully, obscured by the chest compression artifacts.

FIG. 10C is a time diagram of an ECG signal having QRS complexes and chest compression artifacts with a filter mechanism, such as the filter mechanism 425 of FIG. 4, applied thereto. The effect of such application is readily apparent. Indeed, the time diagram of FIG. 10C is significantly closer in appearance to the time diagram of FIG. 10A than to the time diagram of FIG. 10B. One can even readily discern P-waves and inverted T-waves in the time diagram. Further, a QRS detector could use the filtered waveform to provide an accurate intrinsic heart rate indication during delivery of chest compressions to the patient.

FIG. 11A is a time diagram of an ECG signal having no QRS complexes and no chest compression artifacts. For example, the ECG signal of FIG. 11A may generally correspond to a patient, such as the patient 482 of FIG. 4, that is currently experiencing asystole but to whom chest compressions have not yet been applied, e.g., from a chest compression device such as the mechanical chest compression device 485 of FIG. 4.

FIG. 11B is a time diagram of an ECG signal having no QRS complexes and chest compression artifacts with no filtering. For example, the ECG signal of FIG. 11B may generally correspond to a patient, such as the patient 482 of FIG. 4, that is currently experiencing asystole and to whom chest compressions are being concurrently applied, e.g., from a chest compression device such as the mechanical chest compression device 485 of FIG. 4.

FIG. 11C is a time diagram of an ECG signal having no QRS complexes and chest compression artifacts with a filter mechanism, such as the filter mechanism 425 of FIG. 4, applied thereto. As with the time diagram of FIG. 10C, the effect of such application is readily apparent here. Indeed, the time diagram of FIG. 10C is significantly closer in appearance to the time diagram of FIG. 10A than to the time diagram of FIG. 10B.

FIG. 12A is a time diagram of a VF signal having no chest compression artifacts. For example, the VF signal may generally correspond to a patient, such as the patient 482 of FIG. 4, that is currently experiencing VF but to whom chest compressions have not yet been applied, e.g., from a chest compression device 485 of FIG. 4.

FIG. 12B is a time diagram of a VF signal having chest compression artifacts with no filtering For example, the VF signal may generally correspond to a patient, such as the patient 482 of FIG. 4, that is currently experiencing VF and to whom chest compressions are being concurrently applied, e.g., from a chest compression device such as the mechanical chest compression device 485 of FIG. 4.

FIG. 12C is a time diagram of a VF signal having chest compression artifacts with a filter mechanism, such as the filter mechanism 425 of FIG. 4, applied thereto. As with the time diagrams of FIGS. 10C and 11C, the effect of such application is readily apparent here. Indeed, the signal presented by the time diagram of FIG. 10C is significantly closer in appearance to the signal presented by the time diagram of FIG. 10A than to the signal presented by the time diagram of FIG. 10B.

The functions of this description may be implemented by one or more devices that include logic circuitry. The device performs functions and/or methods as are described in this document. The logic circuitry may include a processor that may be programmable for a general purpose, or dedicated, such as microcontroller, a microprocessor, a Digital Signal Processor (DSP), etc. For example, the device may be a digital computer like device, such as a general-purpose computer selectively activated or reconfigured by a computer program stored in the computer. Alternately, the device may be implemented by an Application Specific Integrated Circuit (ASIC), etc.

Moreover, methods are described below. The methods and algorithms presented herein are not necessarily inherently associated with any particular computer or other apparatus. Rather, various general-purpose machines may be used with programs in accordance with the teachings herein, or it may prove more convenient to construct more specialized apparatus to perform the required method steps. The required structure for a variety of these machines will become apparent from this description.

In all cases there should be borne in mind the distinction between methods in this description, and the method of operating a computing machine. This description relates both to methods in general, and also to steps for operating a computer and for processing electrical or other physical signals to generate other desired physical signals.

Programs are additionally included in this description, as are methods of operation of the programs. A program is generally defined as a group of steps leading to a desired result, due to their nature and their sequence. A program is usually advantageously implemented as a program for a computing machine, such as a general-purpose computer, a special purpose computer, a microprocessor, etc.

Storage media are additionally included in this description. Such media, individually or in combination with others, have stored thereon instructions of a program made according to the invention. A storage medium according to the invention is a computer-readable medium, such as a memory, and is read by the computing machine mentioned above.

Performing the steps or instructions of a program requires physical manipulations of physical quantities. Usually, though not necessarily, these quantities may be transferred, combined, compared, and otherwise manipulated or processed according to the instructions, and they may also be stored in a computer-readable medium. These quantities include, for example electrical, magnetic, and electromagnetic signals, and also states of matter that can be queried by such signals. It is convenient at times, principally for reasons of common usage, to refer to these quantities as bits, data bits, samples, values, symbols, characters, images, terms, numbers, or the like. It should be borne in mind, however, that all of these and similar terms are associated with the appropriate physical quantities, and that these terms are merely convenient labels applied to these physical quantities, individually or in groups.

This detailed description is presented largely in terms of flowcharts, display images, algorithms, and symbolic representations of operations of data bits within at least one computer readable medium, such as a memory. Indeed, such descriptions and representations are the type of convenient labels used by those skilled in programming and/or the data processing arts to effectively convey the substance of their work to others skilled in the art. A person skilled in the art of programming may use these descriptions to readily generate specific instructions for implementing a program according to the present invention.

Often, for the sake of convenience only, it is preferred to implement and describe a program as various interconnected distinct software modules or features, individually and collectively also known as software. This is not necessary, however, and there may be cases where modules are equivalently aggregated into a single program with unclear boundaries. In any event, the software modules or features of this description may be implemented by themselves, or in combination with others. Even though it is said that the program may be stored in a computer-readable medium, it should be clear to a person skilled in the art that it need not be a single memory, or even a single machine. Various portions, modules or features of it may reside in separate memories, or even separate machines. The separate machines may be connected directly, or through a network, such as a local access network (LAN), or a global network, such as the Internet.

It will be appreciated that some of these methods may include software steps that may be performed by different modules of an overall software architecture. For example, data forwarding in a router may be performed in a data plane, which consults a local routing table. Collection of performance data may also be performed in a data plane. The performance data may be processed in a control plane, which accordingly may update the local routing table, in addition to neighboring ones. A person skilled in the art will discern which step is best performed in which plane.

An economy is achieved in the present document in that a single set of flowcharts is used to describe both programs, and also methods. So, while flowcharts are described in terms of boxes, they can mean both method and programs.

For this description, the methods may be implemented by machine operations. In other words, embodiments of programs are made such that they perform methods of the invention that are described in this document. These may be optionally performed in conjunction with one or more human operators performing some, but not all of them. As per the above, the users need not be collocated with each other, but each only with a machine that houses a portion of the program. Alternately, some of these machines may operate automatically, without users and/or independently from each other.

Methods are now described.

FIG. 13 is a flowchart 1300 for illustrating methods according to embodiments. The methods of flowchart 1300 may be practiced by systems, devices, and software according to embodiments. For example, the methods illustrated by flowchart 1300 can be performed by the external medical device 400 illustrated in FIG. 4.

According to an operation at 1302, a signal containing ECG data for a patient receiving chest compressions from a mechanical chest compression device is received. The mechanical chest compression device has a chest compression frequency f. Certain embodiments may include detecting the chest compressions being delivered to the patient.

According to an optional operation at 1304, the mechanical chest compression device is identified. In certain embodiments, a processor, such as the processor 430 of FIG. 4, may perform the identifying. In other embodiments, the chest compression device may send identifying information to the processor.

According to a next operation at 1306, at least one filter mechanism is selected. The selecting may be based on a chest compression rate, a sample rate of the ECG data, an identification of the mechanical chest compression device being used to deliver the chest compressions to the patient, or a combination thereof.

The at least one filter mechanism may include a comb filter, an inverse comb filter, a matched filter, a plurality of notch filters, or any suitable combination thereof. In embodiments including a comb filter, the comb filter may be non-adaptive. In embodiments including a plurality of notch filters, each of the notch filters may be non-adaptive.

According to a next operation at 1308, the at least one filter mechanism selected at 1306 is applied to the received signal to at least substantially remove chest compression artifacts from the ECG data, wherein the chest compression artifacts correspond to the chest compressions being delivered to the patient by the mechanical chest compression device.

According to a next operation at 1310, the filtered ECG data may be visually presented to a user, e.g., via a display such as the display 470 illustrated in FIG. 4.

According to an optional operation at 1312, the filtered ECG data is analyzed. Any of a wide variety of suitable techniques may be used in the analyzing.

According to an optional operation at 1314, a shock/no shock decision is determined based on the analyzing. For example, a shock decision may be determined based on a result of the analyzing that indicates no QRS complexes are present in the filtered ECG data. Conversely, a no shock decision may be determined based on a result of the analyzing that indicates QRS complexes are present in the filtered ECG data.

In certain embodiments, methods may further include storing an electrical charge and guiding via electrodes the stored electrical charge to the patient.

Figure 14:
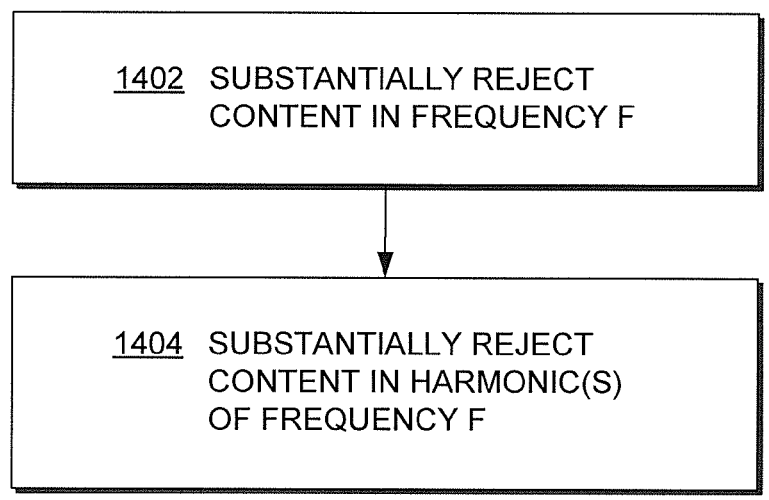
FIG. 14 is a flowchart for illustrating other methods according to embodiments.

FIG. 14 is a flowchart 1400 for illustrating other methods according to embodiments. In particular, the flowchart 1400 corresponds to the operation 1308 of the methods illustrated by the flowchart 1300 of FIG. 13.

According to an operation at 1402, content in the frequency f is substantially rejected by the at least one filter mechanism. Consequently, an amplitude of chest compression artifacts at the frequency f may be reduced, e.g., by at least 20 dB relative to the input signal.

According to a next operation at 1404, content in at least one more frequency that is a higher harmonic to the frequency f is substantially rejected by the at least one filter mechanism. As with the content in the frequency f, an amplitude of chest compression artifacts at each higher harmonic to the frequency f may be reduced, e.g., by at least 20 dB relative to the input signal.

FIG. 15 is a flowchart for illustrating other methods according to embodiments.

According to an operation at 1502, chest compression artifacts in a signal containing ECG data for a patient receiving chest compressions from a mechanical chest compression device are evaluated. For example, a pattern of chest compression artifacts corresponding to the chest compressions being delivered to the patient may be determined. The pattern may be based on starting and stopping of the chest compressions being delivered to the patient, for example.

According to an operation at 1504, a determination is made as to whether the pattern matches an existing chest compression signature. Responsive to a determination that the pattern matches an existing chest compression signature, the method proceeds to an operation at 1506; otherwise, the method proceeds to an operation at 1508.

According to the operation at 1506, a filter mechanism, such as the filter mechanism 425 of FIG. 4, is selected based on the existing chest compression signature. In certain embodiments, information corresponding to the pattern may be merged with information corresponding to the predetermined pattern.

According to the operation at 1508, a new chest compression signature is generated based on the pattern.

According to a next operation at 1510, a filter mechanism, such as the filter mechanism 425 of FIG. 4, is selected based on the chest compression signature generated at 1508.

Certain embodiments may include determining whether the mechanical chest compression device is still delivering chest compressions to the patient. These embodiments may further include suppressing the applying responsive to a determination that the mechanical chest compression device is no longer delivering chest compressions to the patient.

Certain embodiments may include monitoring an impedance signal corresponding to the patient. These embodiments may further include applying a signal-averaging filter to the impedance signal to detect a return of spontaneous circulation (ROSC).

In this description, numerous details have been set forth in order to provide a thorough understanding. In other instances, well-known features have not been described in detail in order to not obscure unnecessarily the description.

A person skilled in the art will be able to practice the present invention in view of this description, which is to be taken as a whole. The specific embodiments as disclosed and illustrated herein are not to be considered in a limiting sense. Indeed, it should be readily apparent to those skilled in the art that what is described herein may be modified in numerous ways. For instance, the mechanical chest compression devices described above may operate at different frequencies than those described above, have different tolerance thresholds than those described above, have different harmonics than those described above, or any combination thereof. Indeed, the frequencies, tolerances, harmonics, and any other variables or values pertinent to the disclosed technology that are discussed or otherwise presented herein are provided only as certain examples. Modifications to the disclosed technology can include equivalents to what is described herein. In addition, the invention may be practiced in combination with other systems.

The following claims define certain combinations and subcombinations of elements, features, steps, and/or functions, which are regarded as novel and non-obvious. Additional claims for other combinations and subcombinations may be presented in this or a related document.

What is claimed is:
1. An external medical device, comprising:
a housing;
a memory within the housing; and
a processor within the housing configured to:
   receive an input signal related to a patient receiving chest compressions from a mechanical chest compression device;

cause the memory to store the input signal;
as part of a post-event review, select at least one filter mechanism including a comb filter, the mechanical chest compression device having a chest compression frequency f; and
as another part of the post-event review, apply the at least one filter mechanism to the stored input signal to at least substantially remove chest compression artifacts from the input signal, wherein the chest compression artifacts correspond to the chest compressions being delivered to the patient by the mechanical chest compression device, and wherein the at least one filter mechanism substantially rejects content in the frequency f and substantially rejects content in at least one more frequency that is a higher harmonic to the frequency f but substantially passes frequencies between the frequency f and the higher harmonic.

2. The device of claim 1, further comprising:
a display in connection with the housing.

3. The device of claim 2, in which
the processor is further configured to cause the display to visually present the filtered input signal to a user.

4. The device of claim 1, in which
the filter mechanism substantially rejects content in the frequency f and substantially rejects content in at least two more frequencies that are additional higher harmonics of the frequency f.

5. The device in claim 1, in which
the input signal is an ECG signal.

6. The device in claim 1, in which
the input signal is an impedance signal.

7. The device of claim 1, in which
the processor is further configured to select at least one filter mechanism responsive to an indication of the mechanical chest compression device being used to deliver the chest compressions to the patient.

8. The device of claim 1, further comprising:
an energy storage module within the housing configured to store an electrical charge, and
a defibrillation port configured to guide via electrodes the stored electrical charge to the patient.

9. The device of claim 1, in which
the processor is configured to receive an indication of the frequency f from the mechanical chest compression device.

10. The device of claim 1, in which
the at least one filter mechanism further comprise a plurality of notch filters.

11. The device of claim 10, in which
the at least one filter mechanism has a Q value of no less than 4.

12. The device of claim 10, in which
the plurality of notch filters has a 3 dB notch width of no more than approximately 0.5 Hz.

13. The device of claim 1, in which
the at least one filter mechanism includes a non-adaptive filter.

14. The device of claim 1, in which
the processor is further configured to detect the chest compressions being delivered to the patient.

15. The device of claim 1, in which
the processor is preconfigured to apply the at least one filter mechanism.

16. The device of claim 1, in which
the processor is configured to apply the at least one filter mechanism to the input signal responsive to input received from a user.

17. The device of claim 1, in which
the processor is configured to select the at least one filter mechanism responsive to input received from a user.

18. The device of claim 1, in which
the processor is configured to select the at least one filter mechanism responsive to input received from the mechanical chest compression device delivering the chest compressions to the patient.

19. The device of claim 1, in which
the processor is further configured to suppress application of the at least one filter mechanism to the input signal responsive to a determination that the mechanical chest compression device is no longer delivering chest compressions to the patient.

20. The device of claim 1, in which
the processor is further configured to monitor an impedance signal corresponding to the patient.

21. The device of claim 20, in which
the processor is further configured to detect return of spontaneous circulation (ROSC) by applying the at least one filter mechanism to the impedance signal.

22. A method in an external medical device, the method comprising:
receiving an input signal related to a patient receiving chest compressions from a mechanical chest compression device, the mechanical chest compression device having a chest compression frequency f and the input signal having been stored in a memory;
as part of a post-event review, selecting at least one filter mechanism that includes a comb filter; and
as another part of the post-event review, applying the at least one filter mechanism to the received signal to at least substantially remove chest compression artifacts therefrom, wherein the chest compression artifacts correspond to the chest compressions being delivered to the patient by the mechanical chest compression device, and wherein the applying includes:
substantially rejecting content in the frequency f by the at least one filter mechanism, and
substantially rejecting content in at least one more frequency that is a higher harmonic to the frequency f by the at least one filter mechanism.

23. The method of claim 22, in which
the receiving, selecting, and applying are each part of the post-event review.

24. The method of claim 22, in which
the input signal is an ECG signal.

25. The method of claim 22, in which
the input signal is an impedance signal.

26. The method of claim 22, further comprising:
visually presenting the filtered received signal to a user.

27. The method of claim 22, in which
the selecting is based on a chest compression rate, a sample rate of the input signal, an identification of the mechanical chest compression device being used to deliver the chest compressions to the patient, or a combination thereof.

28. The method of claim 22, further comprising:
storing an electrical charge, and
guiding via electrodes the stored electrical charge to the patient.

29. The method of claim 22, further comprising:
detecting the chest compressions being delivered to the patient.

30. The method of claim 22, further comprising:
determining whether the mechanical chest compression device is delivering chest compressions to the patient.

31. The method of claim 30, further comprising:
suppressing the applying responsive to a determination that the mechanical chest compression device is no longer delivering chest compressions to the patient.

32. The method of claim 22, further comprising:
monitoring an impedance signal corresponding to the patient.

33. The method of claim 32, further comprising:
applying a signal-averaging filter to the impedance signal to detect a return of spontaneous circulation (ROSC).

34. The method of claim 22, in which
the comb filter is non-adaptive.

35. The method of claim 22, in which
the at least one filter mechanism further comprises a plurality of notch filters.

36. The method of claim 35, in which
each of the notch filters is non-adaptive.

37. The device of claim 7, in which the indication is an identification.

* * * * *